(12) United States Patent
Babiker et al.

(10) Patent No.: US 12,128,071 B1
(45) Date of Patent: Oct. 29, 2024

(54) METHOD OF TREATING ILLNESS USING LYOPHILIZED CAMEL URINE

(71) Applicant: KING FAISAL UNIVERSITY, Al-Ahsa (SA)

(72) Inventors: Marwa Abdelgader Mustafa Babiker, Al-Ahsa (SA); Salwa Mohamed Elbashir, Al-Ahsa (SA)

(73) Assignee: KING FAISAL UNIVERSITY, Al-Ahsa (SA)

( * ) Notice: Subject to any disclaimer, the term of this patent is extended or adjusted under 35 U.S.C. 154(b) by 0 days.

(21) Appl. No.: 18/391,194

(22) Filed: Dec. 20, 2023

(51) Int. Cl.
*A61K 35/22* (2015.01)
*A61K 9/19* (2006.01)

(52) U.S. Cl.
CPC ............... *A61K 35/22* (2013.01); *A61K 9/19* (2013.01)

(58) Field of Classification Search
CPC .................................. A61K 35/22; A61K 9/19
See application file for complete search history.

(56) References Cited

U.S. PATENT DOCUMENTS

2002/0164378 A1   11/2002   Singh et al.

FOREIGN PATENT DOCUMENTS

CN   102000112 A   *   4/2011

OTHER PUBLICATIONS

Al Neyadi et al, The effect of camel urine on islet morphology and CCL4-induced liver cirrhosis in rat. BMC Proceedings, (Jul. 9, 2012) vol. 6, Supp. SUPPL. 4. Abstract No. P42 (Year: 2012).*
Abdelzaher et al., "Evaluation of the Effectiveness of Virgin Camel's Urine as Antifungal Agents", Journal of Bacteriology & Mycology, vol. 8 Issue 4, Nov. 13, 2020, pp. 124-128.
Salwa et al., "Novel Compounds in Lyophilized Female Camel Urine", Journal of Infectious Diseases and Therapy, vol. 4, issue 5, Oct. 17, 2016.

* cited by examiner

*Primary Examiner* — Qiuwen Mi
(74) *Attorney, Agent, or Firm* — Nath, Goldberg & Meyer; Joshua B. Goldberg

(57) ABSTRACT

A method of treating illness is provided by collecting urine of a virgin female camel, performing lyophilization on the urine to form dehydrated urine, forming a medicament using the dehydrated urine as an active ingredient, and administering the medicament to a patient. The medicament can be a nutritional drink, an edible jam, an oral syrup, a suppository, a topical moisturizer, or an injection. The pharmaceutical composition comprises an active ingredient derived from lyophilized urine of a virgin female camel, a pharmaceutical carrier, and one or more additional excipients. The pharmaceutical composition can be used to treat hepatitis B and C, schistosomiasis, fascicola infections, rectal hemorrhoids, and ringworm.

9 Claims, 4 Drawing Sheets

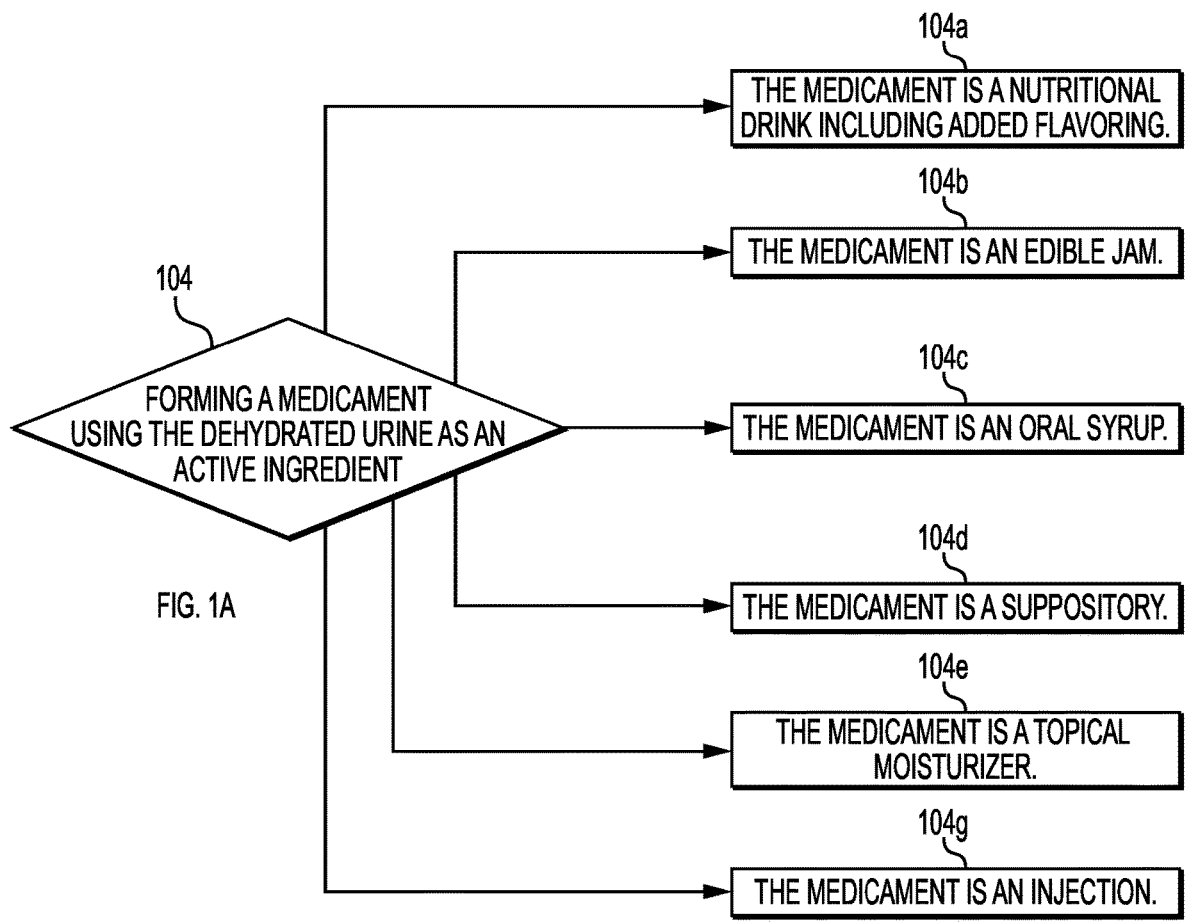

METHOD OF TREATING ILLNESS USING LYOPHILIZED CAMEL URINE

BACKGROUND

Field

The disclosure of the present patent application relates to methods for treating illnesses, and particularly to a method for treating illness involving the use of urine from a virgin female camel.

Description of Related Art

In the field of medicine and health supplements, various natural substances have been explored for their potential health benefits. One such substance that has been traditionally used in Muslim cultures is camel urine. However, the use of camel urine in its raw form has several challenges. Some may find the use of camel urine in its raw form to be unpalatable. Moreover, the raw urine needs to be collected and stored properly to prevent contamination. Furthermore, the dosage of the urine to be consumed or applied is also a challenge as it varies depending on the individual patient and the specific ailment being treated. Therefore, there is a need for a more convenient and standardized way to utilize the potential health benefits of camel urine, as well as methods of preparation and administration that are palatable and convenient for patients.

SUMMARY OF THE INVENTION

In accordance with embodiments, a method is provided for treating illness. The method involves collecting urine of a virgin female camel, performing lyophilization on the urine to form dehydrated urine, forming a medicament using the dehydrated urine as an active ingredient, and administering the medicament to a patient. The medicament can be a nutritional drink, an edible jam, an oral syrup, a suppository, a topical moisturizer, or an injection.

In accordance with other embodiments, a pharmaceutical composition is provided. The composition comprises an active ingredient derived from lyophilized urine of a virgin female camel, a pharmaceutical carrier, and one or more additional excipients. The pharmaceutical composition can be used for treating hepatitis B and C, schistosomiasis, fascicola infections, rectal hemorrhoids, and ringworm in a patient. These and other features of the present subject matter will become readily apparent upon further review of the following specification.

BRIEF DESCRIPTION OF DRAWINGS

FIG. 1A illustrates sub-steps of using dehydrated urine as an active ingredient from the method of FIG. 1.

Similar reference characters denote corresponding features consistently throughout the attached drawings.

DETAILED DESCRIPTION

Definitions

Figure 1:
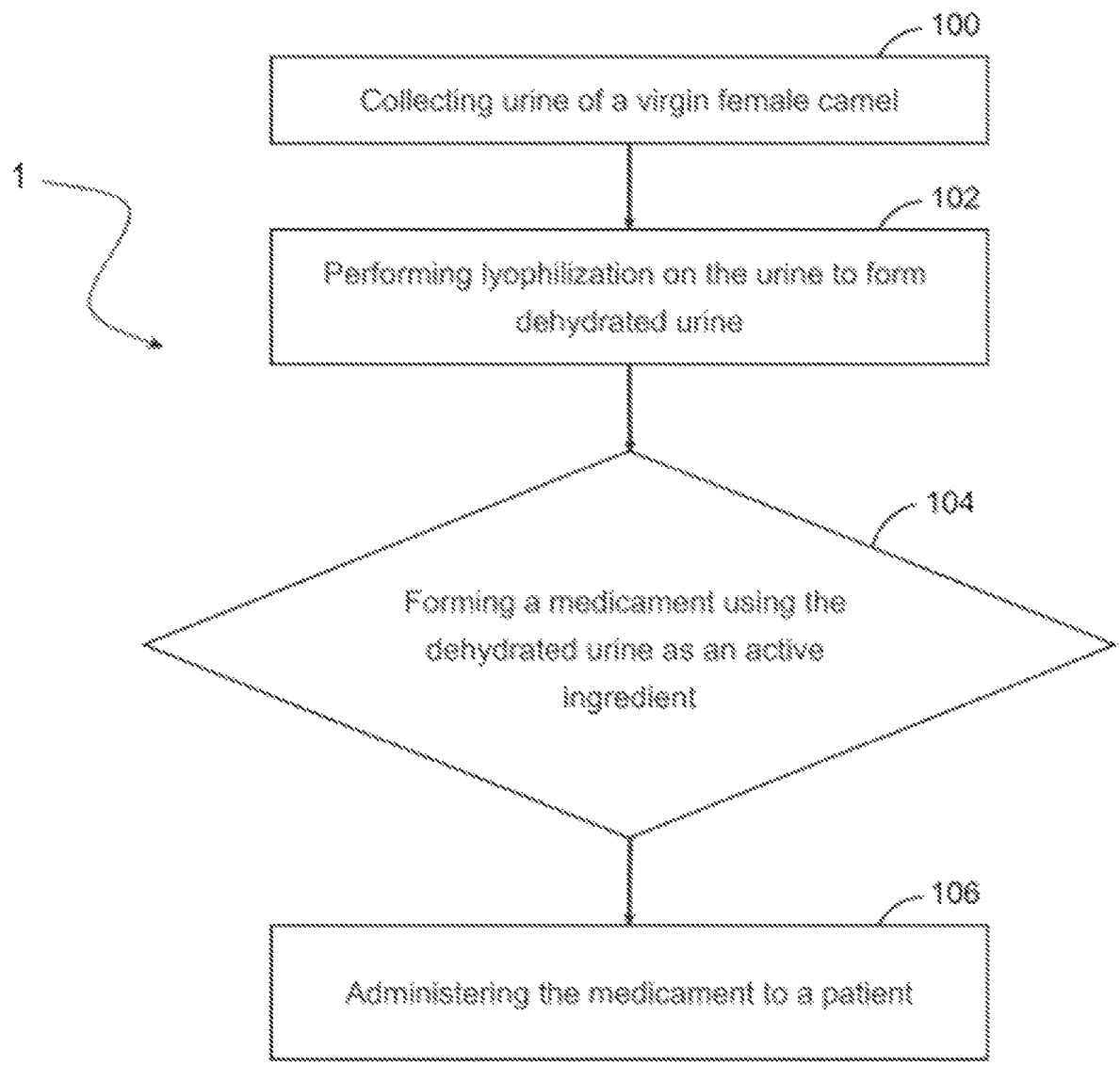
FIG. 1 illustrates a process of treating illnesses using a medicament made from dehydrated camel urine.

It should be understood that the drawings described above or below are for illustration purposes only with emphasis generally being placed upon illustrating the principles of the present teachings. The drawings are not intended to limit the scope of the present teachings in any way.

Throughout the application, where compositions are described as having, including, or comprising specific components, or where processes are described as having, including, or comprising specific process steps, it is contemplated that compositions of the present teachings can also consist essentially of, or consist of, the recited components, and that the processes of the present teachings can also consist essentially of, or consist of, the recited process steps.

It is noted that, as used in this specification and the appended claims, the singular forms "a", "an", and "the" include plural references unless the context clearly dictates otherwise.

In the application, where an element or component is said to be included in and/or selected from a list of recited elements or components, it should be understood that the element or component can be any one of the recited elements or components, or the element or component can be selected from a group consisting of two or more of the recited elements or components. Further, it should be understood that elements and/or features of a composition or a method described herein can be combined in a variety of ways without departing from the spirit and scope of the present teachings, whether explicit or implicit herein.

The use of the terms "include," "includes", "including," "have," "has," or "having" should be generally understood as open-ended and non-limiting unless specifically stated otherwise.

The use of the singular herein includes the plural (and vice versa) unless specifically stated otherwise. In addition, where the use of the term "about" or "approximately" is before a quantitative value, the present teachings also include the specific quantitative value itself, unless specifically stated otherwise. As used herein, the term "about" or "approximately" refers to a ±10% variation from the nominal value unless otherwise indicated or inferred.

The term "optional" or "optionally" means that the subsequently described event or circumstance may or may not occur, and that the description includes instances where said event or circumstance occurs and instances in which it does not.

Unless defined otherwise, all technical and scientific terms used herein have the same meaning as commonly understood to one of ordinary skill in the art to which the presently described subject matter pertains.

Where a range of values is provided, for example, concentration ranges, percentage ranges, or ratio ranges, it is understood that each intervening value, to the tenth of the unit of the lower limit, unless the context clearly dictates otherwise, between the upper and lower limit of that range and any other stated or intervening value in that stated range, is encompassed within the described subject matter. The upper and lower limits of these smaller ranges may independently be included in the smaller ranges, and such embodiments are also encompassed within the described subject matter, subject to any specifically excluded limit in the stated range. Where the stated range includes one or both of the limits, ranges excluding either or both of those included limits are also included in the described subject matter.

Throughout the application, descriptions of various embodiments use "comprising" language. However, it will be understood by one of skill in the art, that in some specific instances, an embodiment can alternatively be described using the language "consisting essentially of" or "consisting of".

For purposes of better understanding the present teachings and in no way limiting the scope of the teachings, unless otherwise indicated, all numbers expressing quantities, percentages or proportions, and other numerical values used in the specification and claims, are to be understood as being modified in all instances by the term "about" or "approximately". Accordingly, unless indicated to the contrary, the numerical parameters set forth in the following specification and attached claims are approximations that may vary depending upon the desired properties sought to be obtained. At the very least, each numerical parameter should at least be construed in light of the number of reported significant digits and by applying ordinary rounding techniques.

With reference to FIG. 1, a method 1 is shown of a first embodiment of the present disclosure. Step 100 involves the collection of urine from a virgin female camel. The urine of a virgin female camel is chosen due to its properties that are beneficial for treating various illnesses. The collection process involves obtaining the urine in a hygienic manner to ensure that it is free from any contaminants. The collected urine undergoes lyophilization in Step 102. Lyophilization, also known as freeze-drying, is a process that removes water from the urine, resulting in dehydrated urine. This process concentrates the beneficial components of the urine, enhancing its potency for treatment purposes. The process of lyophilization of the urine involves reducing the surrounding pressure and adding enough heat to allow the frozen water in the material to sublimate directly from the solid phase to the gas phase. The dehydrated urine is then used to form a medicament in Step 104.

With reference to FIG. 1A, the medicament serves as an active ingredient in various forms of treatment. The medicament can take forms including a nutritional drink supplement 104a, an edible jam 104b, an oral syrup 104c, a suppository 104d, a topical moisturizer 104e, or an injection 104f. Each form of treatment catering to different types of illnesses and patient preferences.

Figure 1B:
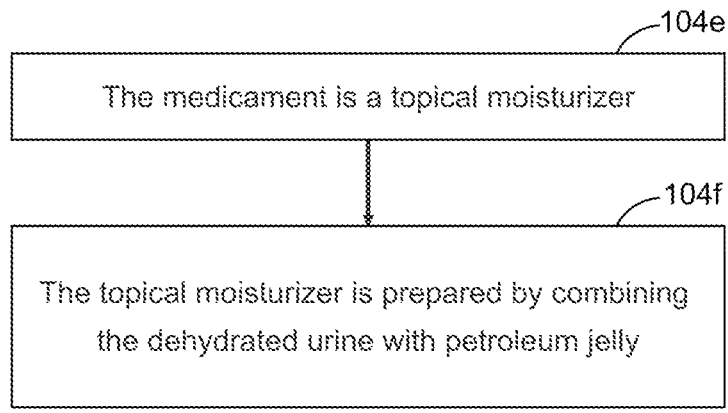
FIG. 1B illustrates sub-steps of forming a topical moisturizer medicament from the process of FIG. 1A.

Turning to FIG. 1B, in the case of the medicament being used as a topical moisturizer 104e, sub-step 104f includes forming the topical moisturizer by combining the dehydrated urine with petroleum jelly. The ratio of dehydrated urine to petroleum jelly is about 2 g for 100 ml of petroleum jelly, or about 2% w/v.

Figure 1C:
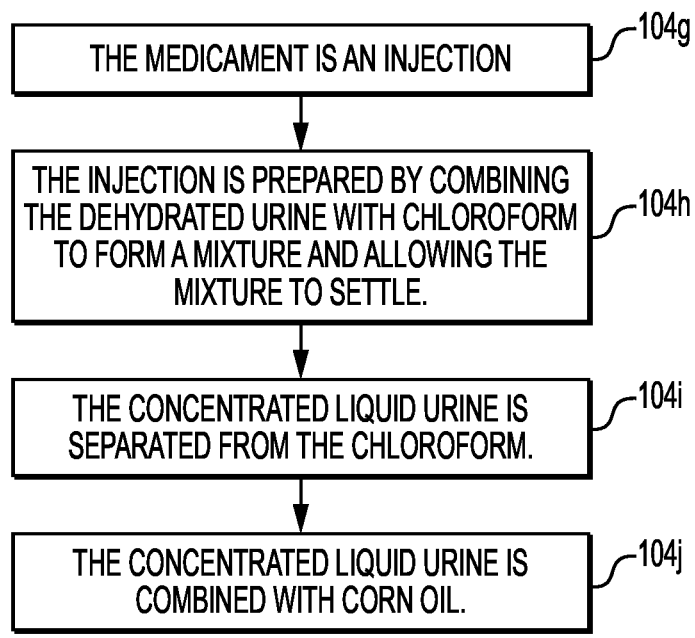
FIG. 1C illustrates sub-steps of forming an injection medicament from the process of FIG. 1A.

With reference to FIG. 1C, in the case of the medicament being used as an injection in Sub-step 104g, Sub-steps 104h-j are included to convert the solid, dehydrated urine into a concentrated liquid injection. Sub-step 104h involves combining the dehydrated urine with a solvent to form a mixture in a ratio of about 1:1, and letting the mixture settle for a time period of about three hours. In a non-limiting example, the solvent chosen for dissolving the dehydrated urine is chloroform. Next, in Sub-step 104i, the concentrated liquid urine is separated from the chloroform using, for example, a separator funnel. The concentrated liquid is next combined with a carrier, such as corn oil, in a weight ratio of about 1:2 to form an injectable liquid.

Referring again to FIG. 1, the medicament is administered to a patient as per Step 106. The method of administration depending on the particular form of the medicament, such as ingestion of the nutritional drink supplement, edible jam, and/or oral syrup, rectal insertion of the suppository, topical administration of the moisturizer to the skin, and injection of the medicament as a vaccine. The dosage of the medicament is determined based on the patient's body weight, with an average dose found through experimentation to be approximately 250 mg of the lyophilized active ingredient per 1 kg of a patient's body weight. Thus, for an average adult of 70 kg, the daily recommended dose would be about 17500 mg, which may be spread out evenly in interval dosages, or effective amounts, throughout the day. For example, effective amounts could include 3,500 mg 5×/day, 4,375 mg 4×/day, etc taken by dividing the average daily dose of 17500 mg by a chosen daily interval (5×/day, 4×/day, 3×/day, etc.).

Figure 2:
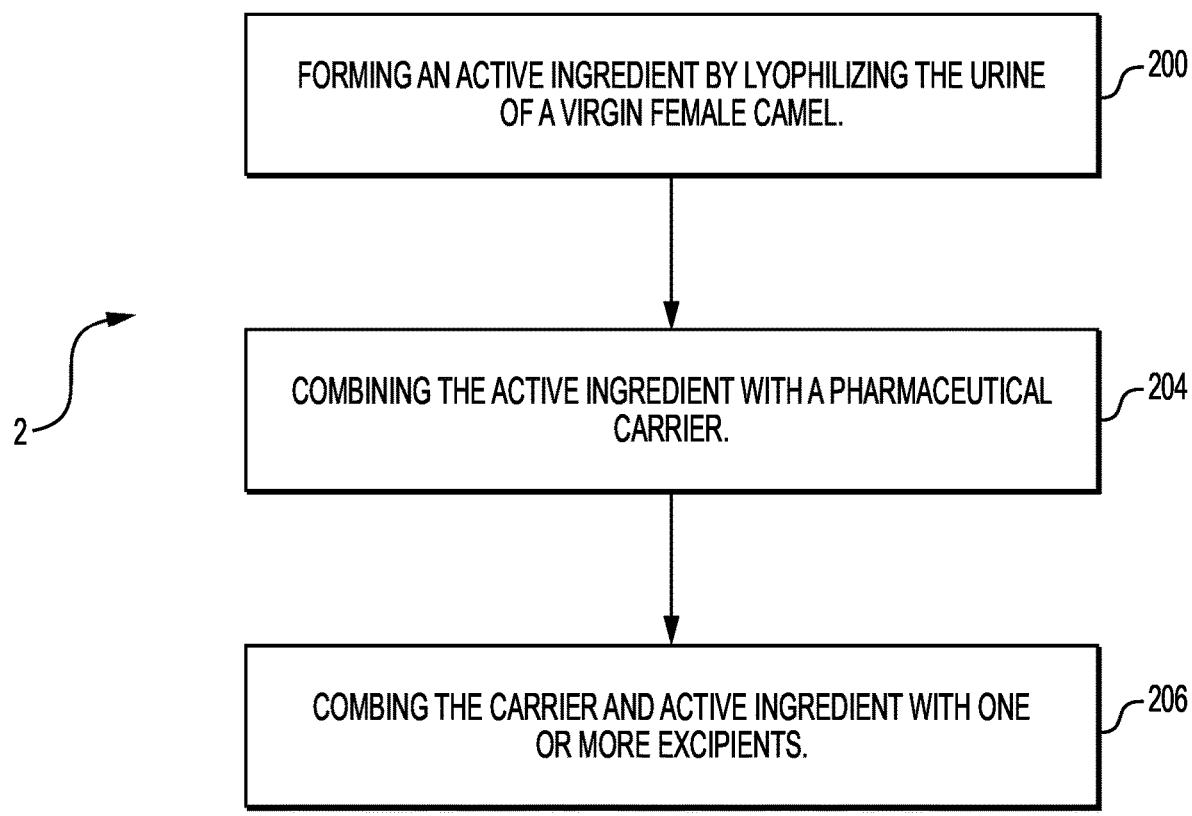
FIG. 2 illustrates a process of forming a pharmaceutical composition using lyophilized urine of a virgin female camel.

In accordance with other embodiments, a pharmaceutical composition and method of producing are provided. Referring to FIG. 2, the method 2 of forming a pharmaceutical composition involves forming an active ingredient derived from lyophilized urine of a virgin female camel at step 200 and combining the active ingredient with a pharmaceutical carrier at step 204. A carrier is a specific type of ingredient added to a pharmaceutical composition not intended to have a therapeutic effect. Carriers may act as vehicles for the active ingredient, assisting in its solubility, absorption, or controlled release. In the case of edibles, nutritional drinks, oral syrups, and jams, carriers may include liquid bases formed from water or juice. In the case of suppositories, carriers may include fatty or hydrophilic bases, vegetable oils, glycerides, among others. In the case of injections, carriers may include purified water, oils such as corn, sesame, and cottonseed, among others. In the case of topical medicaments, carriers would include petroleum or other oily bases.

Continuing with FIG. 2, the pharmaceutical composition is formed in step 206 by combining the active ingredient and carrier with one or more excipients. An excipient includes an inactive substance added to the pharmaceutical composition not intended to have a therapeutic effect and included for purposes such as aiding in formulation, improving stability, enhancing bioavailability, or providing a specific physical characteristic. Example excipients would generally include fillers or diluents, binders, flavors and sweeteners, preservatives, pH adjusters, ointments and colorants.

The pharmaceutical composition formed by the method of FIG. 2 can be used for treating hepatitis B and C in the form of an injectable vaccination. The pharmaceutical composition can be used for treatment of schistosomiasis and fascicola infections in the form of an oral syrup. The pharmaceutical composition can further be used for the treatment of rectal hemorrhoids in the form of a suppository. The pharmaceutical composition can be used to heal infections to the liver in the form of a nutritional drink. In addition, the pharmaceutical composition can be used for the treatment of ringworm in the form of a topical moisturizer or medicament.

It is to be understood that the method of treating illness is not limited to the specific embodiments described above, but encompasses any and all embodiments within the scope of the generic language of the following claims enabled by the embodiments described herein, or otherwise shown in the drawings or described above in terms sufficient to enable one of ordinary skill in the art to make and use the claimed subject matter.

The invention claimed is:

1. A method of treating illness, comprising:
   collecting urine of a virgin female camel;
   performing lyophilization on the urine to form dehydrated urine;
   forming a medicament using the dehydrated urine as an active ingredient;
   administering the medicament to a patient in need thereof;
   wherein the illness is selected from the group consisting of hepatitis B, hepatitis C, schistosomiasis, fasciola, rectal hemorrhoids, and ringworm.

2. The method of treating illness as recited in claim 1, wherein the medicament is a nutritional drink including added flavoring.

3. The method of treating illness as recited in claim 1, wherein the medicament is an edible jam.

4. The method of treating illness as recited in claim 1, wherein the medicament is an oral syrup.

5. The method of treating illness as recited in claim 1, wherein the medicament is a suppository.

6. The method of treating illness as recited in claim 1, wherein the medicament is a topical moisturizer.

7. The method of treating illness as recited in claim 6, wherein the topical moisturizer is prepared by combining the dehydrated urine with petroleum jelly in an amount of about 2% w/v.

8. The method of treating illness as recited in claim 1, wherein the medicament is an injection.

9. The method of treating illness as recited in claim 8, wherein the injection is prepared by combining the dehydrated urine with chloroform in a 1:1 ratio to form a mixture; letting the mixture settle for about 3 hours; separating the urine from the chloroform using a separator funnel; and combining the urine with corn oil in a ratio of about 1:2.

* * * * *

UNITED STATES PATENT AND TRADEMARK OFFICE
CERTIFICATE OF CORRECTION

| | |
|---|---|
| PATENT NO. | : 12,128,071 B1 |
| APPLICATION NO. | : 18/391194 |
| DATED | : October 29, 2024 |
| INVENTOR(S) | : Marwa Abdelgader Mustafa Babiker and Salwa Mohamed Elbashir |

It is certified that error appears in the above-identified patent and that said Letters Patent is hereby corrected as shown below:

On the Title Page

Item (12), should read Elbashir et al.

Item (72) please update the order of Inventors to: "Salwa Mohamed Elbashir", "Marwa Abdelgader Mustafa Babiker".

Please remove the residence of the Inventor Salwa Mohamed Elbashir and replace with "Khartoum (SD)".

Signed and Sealed this
Twenty-eighth Day of October, 2025

John A. Squires
*Director of the United States Patent and Trademark Office*